United States Patent

Wincheski et al.

[11] Patent Number: 5,942,894
[45] Date of Patent: Aug. 24, 1999

[54] RADIALLY FOCUSED EDDY CURRENT SENSOR FOR DETECTION OF LONGITUDINAL FLAWS IN METALLIC TUBES

[75] Inventors: Russell A. Wincheski, Williamsburg; John W. Simpson, Tabb; James P. Fulton, Hampton, all of Va.; Shridhar C. Nath, Gaithersburg, Md.; Ronald G. Todhunter, Grafton; Min Namkung, Yorktown, both of Va.

[73] Assignee: The United States of America as represented by the Administrator of the National Aeronautics and Space Administration, Washington, D.C.

[21] Appl. No.: 08/527,741

[22] Filed: Sep. 13, 1995

[51] Int. Cl.⁶ .......................... G01N 27/72; G01R 33/12
[52] U.S. Cl. .......................... 324/220; 324/240
[58] Field of Search .......................... 324/219, 220, 324/221, 239, 240, 241, 242, 243

[56] References Cited

U.S. PATENT DOCUMENTS

| | | | |
|---|---|---|---|
| 2,790,140 | 4/1957 | Bender | 324/220 |
| 3,532,969 | 10/1970 | McCullough et al. | 324/220 |
| 4,629,964 | 12/1986 | Scalese | 324/219 |
| 4,806,863 | 2/1989 | White . | |
| 5,119,023 | 6/1992 | Lloyd | 324/239 |
| 5,493,511 | 2/1996 | Wincheski et al. . | |
| 5,617,024 | 4/1997 | Simpson et al. | 324/241 |
| 5,648,721 | 7/1997 | Wincheski et al. . | |
| 5,698,977 | 12/1997 | Simpson et al. . | |

*Primary Examiner*—Walter E. Snow
*Attorney, Agent, or Firm*—Robin W Edwards

[57] ABSTRACT

A radially focused eddy current sensor detects longitudinal flaws in a metal tube. A drive coil induces eddy currents within the wall of the metal tube. A pick-up coil is spaced apart from the drive coil along the length of the metal tube. The pick-up coil is positioned with one end thereof lying adjacent the wall of the metal tube such that the pick-up coil's longitudinal axis is perpendicular to the wall of the metal tube. To isolate the pick-up coil from the magnetic flux of the drive coil and the flux from the induced eddy currents, except the eddy currents diverted by a longitudinal flaw, an electrically conducting material high in magnetic permeability surrounds all of the pick-up coil except its one end that is adjacent the walls of the metal tube. The electrically conducting material can extend into and through the drive coil in a coaxial relationship therewith.

20 Claims, 7 Drawing Sheets

RADIALLY FOCUSED EDDY CURRENT SENSOR FOR DETECTION OF LONGITUDINAL FLAWS IN METALLIC TUBES

ORIGIN OF THE INVENTION

The invention described herein was jointly made by employees of the United States Government and during the performance of work under NASA contracts and is subject to provisions of Section 305 of the National Aeronautics and Space Act of 1958, as amended, Public Law 85-568 (72 Stat. 435; 42 USC 2457), and 35 USC 202, respectively. In accordance with 35 USC 202, the contractor elected not to retain title.

BACKGROUND OF THE INVENTION

1. Field of the Invention

This invention relates to eddy current sensors. More specifically, the invention is a radially focused eddy current sensor for detecting longitudinal flaws in a metal tube.

2. Description of the Related Art

The inspection of longitudinal welds in metallic tubular structures is a major concern in the nuclear power industry where critical pressure vessels are typically welded together in longitudinal sections. Corrosive environments can speed the degradation of these welds and can limit access thereto for inspection of the welds.

To help overcome these obstacles, eddy current probes have been developed that simply require positioning and moving an eddy current coil in a tubular piece being inspected. However, conventional eddy current probes are based on impedance measurements of the piece being inspected. Such measurements require complicated instrumentation and often provide flaw signatures which are difficult to interpret. This is especially true for differential measurements necessary for most tubing inspections. In addition, the driving fields of the conventional eddy current probe are not focused so that the coupling between the primary field of the probe and the flaw is normally weak. The impedance measurements of eddy current probes are also extremely sensitive to changes in the conductivity and permeability of the piece being inspected. Small changes in these parameters, which are common near weld joints, can therefore disguise the signal due to a fatigue crack.

SUMMARY OF THE INVENTION

Accordingly, it is an object of the present invention to provide a sensor for detecting flaws in longitudinal welds of metallic tubular structures.

Another object of the present invention is to provide a sensor for detecting longitudinal flaws in metallic tubular structures.

Still another object of the present invention is to provide an eddy current sensor for detecting longitudinal flaws in metallic tubular structures.

Other objects and advantages of the present invention will become more obvious hereinafter in the specification and drawings.

In accordance with the present invention, a radially focused eddy current sensor detects longitudinal flaws in a metal tube. A drive coil is sized for longitudinal insertion in the metal tube and is excited by an alternating current source such that the drive coil induces eddy currents within the wall of the metal tube. A pick-up coil is sized for lateral insertion in the metal tube. The pick-up coil is spaced apart from the drive coil along the length of the metal tube. The pick-up coil has a first end plane and a second end plane with a longitudinal axis passing through the first and second end planes. The first end plane is positioned to lie adjacent the wall of the metal tube such that the longitudinal axis is perpendicular to the wall of the metal tube. An electrical measurement device such as a voltmeter is coupled to the pick-up coil for providing an indication of voltage induced across the first end plane of the pick-up coil. To isolate the pick-up coil from the magnetic flux of the drive coil and the flux from the induced eddy currents, except the eddy currents diverted by a longitudinal flaw, an electrically conducting material high in magnetic permeability surrounds all of the pick-up coil except its first end plane. The electrically conducting material can extend into and through the drive coil in a coaxial relationship therewith.

DETAILED DESCRIPTION OF THE INVENTION

Figure 1:
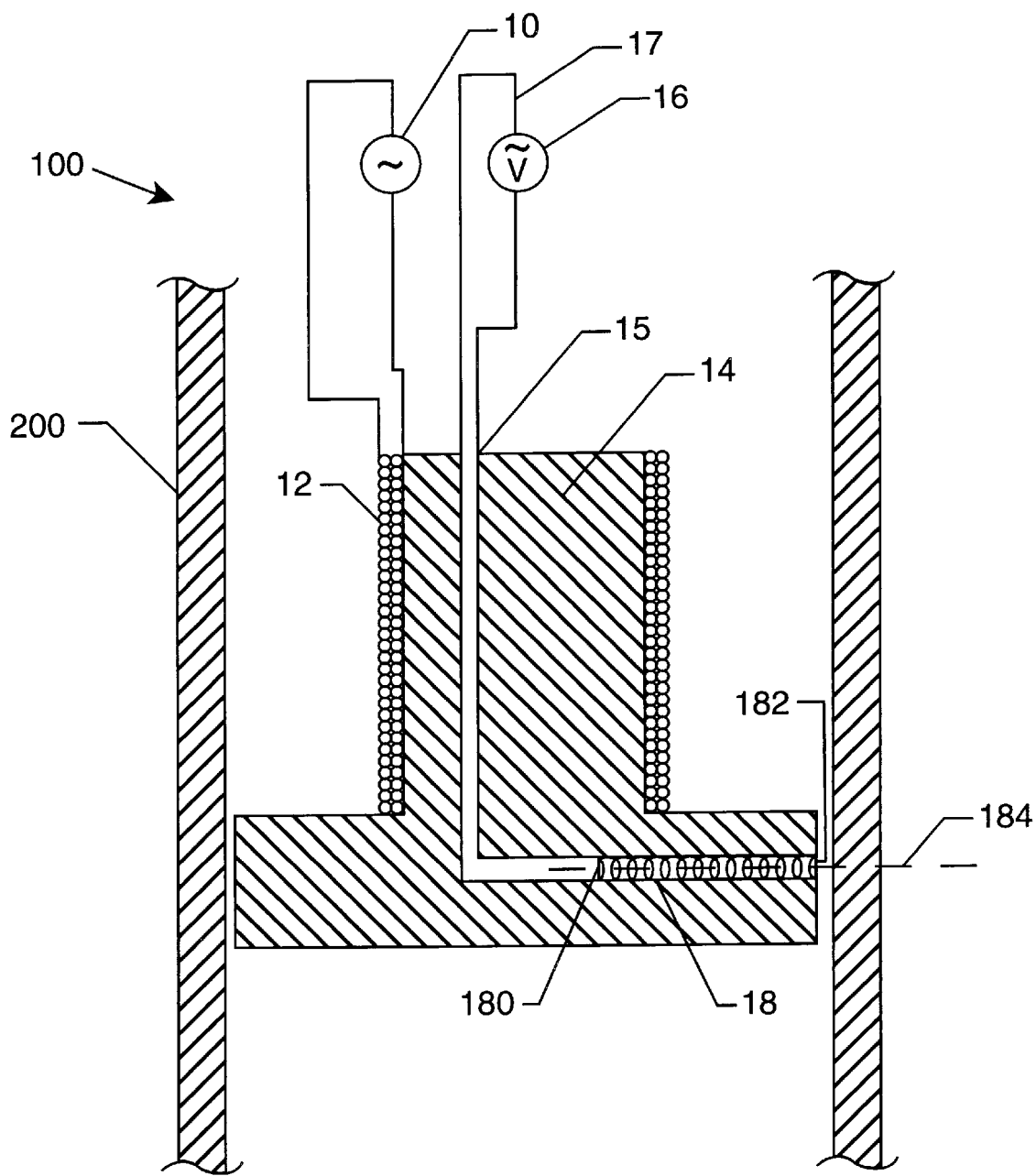
FIG. 1 is in part a cross-sectional view and in part a schematic view of the radially focused eddy current sensor according to one embodiment of the present invention as it is positioned within a section of metal tube.

Referring now to the drawings, and more particularly to FIG. 1, one embodiment of radially focussed eddy current sensor is shown and referenced generally by numeral 100. Sensor 100 is shown positioned within metal tube 200 which represents the test piece that is to be inspected for longitudinal flaws, e.g., material cracks, voids, fatigue cracks at welds or other types of joints, etc.

The component parts of sensor 100 include alternating current (AC) source 10 connected to the windings of magnetizing or drive coil 12 for supplying a sinusoidal current thereto. Drive coil 12 consists of a single or multiple layers (as shown) of windings such that when energized with current from AC source 10, eddy currents are induced in metal tube 200. Drive coil 12 is wound about a cylindrical core of electrically conducting material 14 having properties that will be discussed in greater detail below. In this embodiment, conducting material 14 extends the entire length of drive coil 12.

AC voltmeter 16 has leads 17 passing through a small hole 15 of conducting material 14 for connection to pick-up coil 18 which can be configured as is known in the art.

Pick-up coil 18 is a cylindrical coil defined at either end thereof by end planes 180 and 182, and further defined by longitudinal axis 184 which passes through end planes 180 and 182.

Pick-up coil 18 is spaced apart from drive coil 12 along the length of metal tube 200. Typically, the amount of spacing is on the order of a few hundredths of an inch, e.g., approximately 0.05 inches. As longitudinal spacing between drive coil 12 and pick-up coil 18 increases, sensitivity of sensor 100 decreases. Conducting material 14 encases or surrounds the entirety of pick-up coil 18 except for end plane 182 which is exposed to the environment. As will be explained in greater detail below, conducting material 14 serves to isolate pick-up coil 18 from the magnetic flux produced by drive coil 12 thereby enhancing the sensitivity of pick-up coil 18 to longitudinal flaws in metal tube 200. In addition, the rigid nature of conducting material 14 is useful structurally for establishing the proper positioning of drive coil 12 and pick-up coil 18. More specifically, drive coil 12 is longitudinally aligned within metal tube 200 while pick-up coil 18 is simultaneously laterally positioned in metal tube 200 such that its longitudinal axis 184 is perpendicular to the wall of metal tube 200. To improve isolation of pick-up coil 18 from flux produced by drive coil 12 in order to enhance the sensitivity of sensor 100 to longitudinal flaws, end plane 182 is positioned adjacent and closer to the wall of metal tube 200 than drive coil 12.

Conducting material 14 is typically machined from a single piece of electrically conducting material that is also high in magnetic permeability. For purposes of the present invention, electrically conducting material 14 is defined by a resistivity that does not exceed 100 microhm-centimeters and a relative initial permeability of at least 100. Thus, conducting material 14 can be made from the readily available and inexpensive 10–20 (mild) steel and iron. A variety of other materials are also suitable and can be found listed in "Table 2 Some Properties of High Permeability Materials" of Appendix 4 of "Ferromagnetism" by R. M. Bozorth, IEEE Press, 1978, on pages 870–871, which is hereby incorporated by reference.

Figure 2:
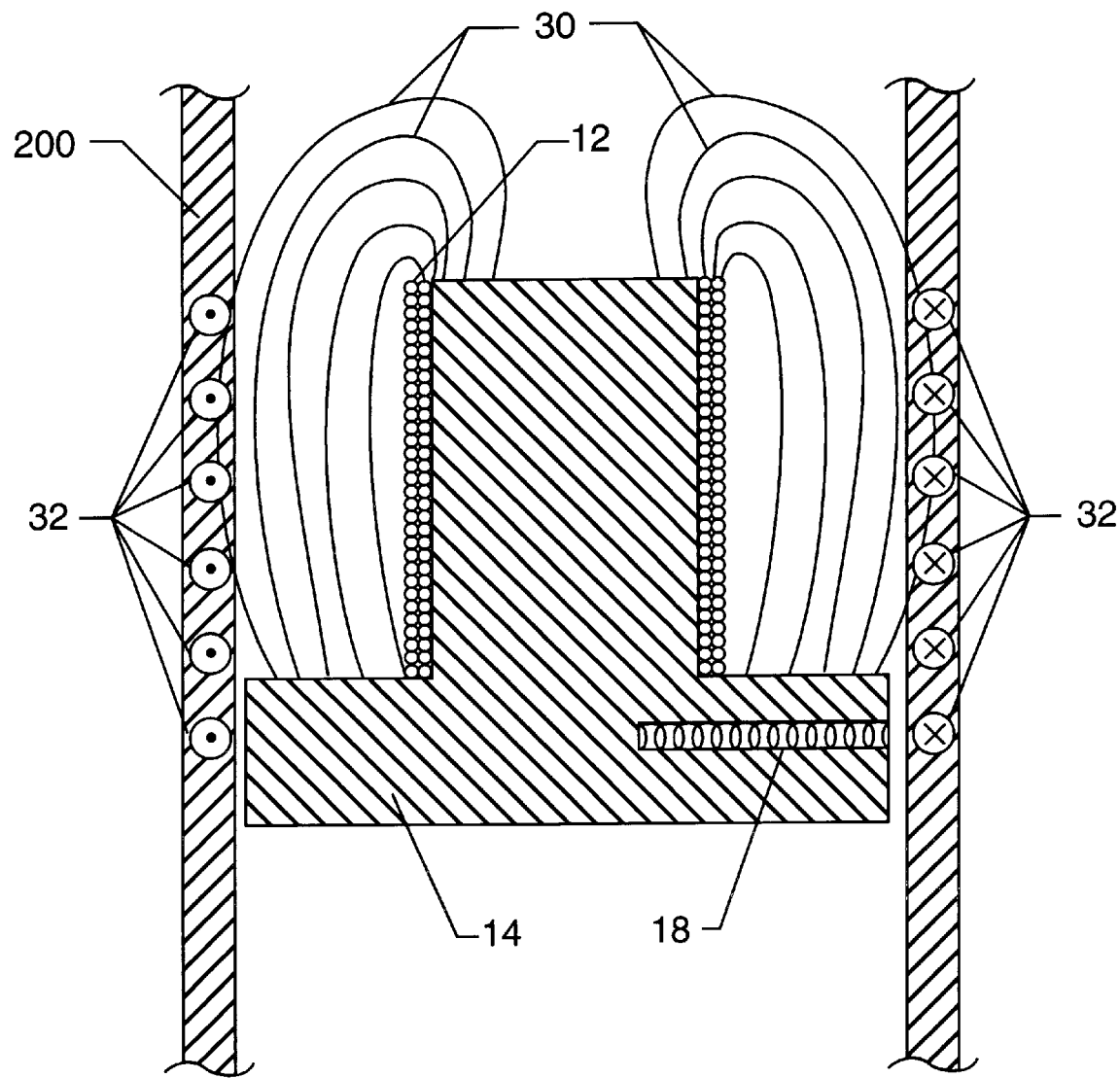
FIG. 2 is the cross-sectional view of the embodiment of FIG. 1 showing the magnetic flux lines and resulting circumferential eddy currents for an unflawed section of tube.
Figure 3:
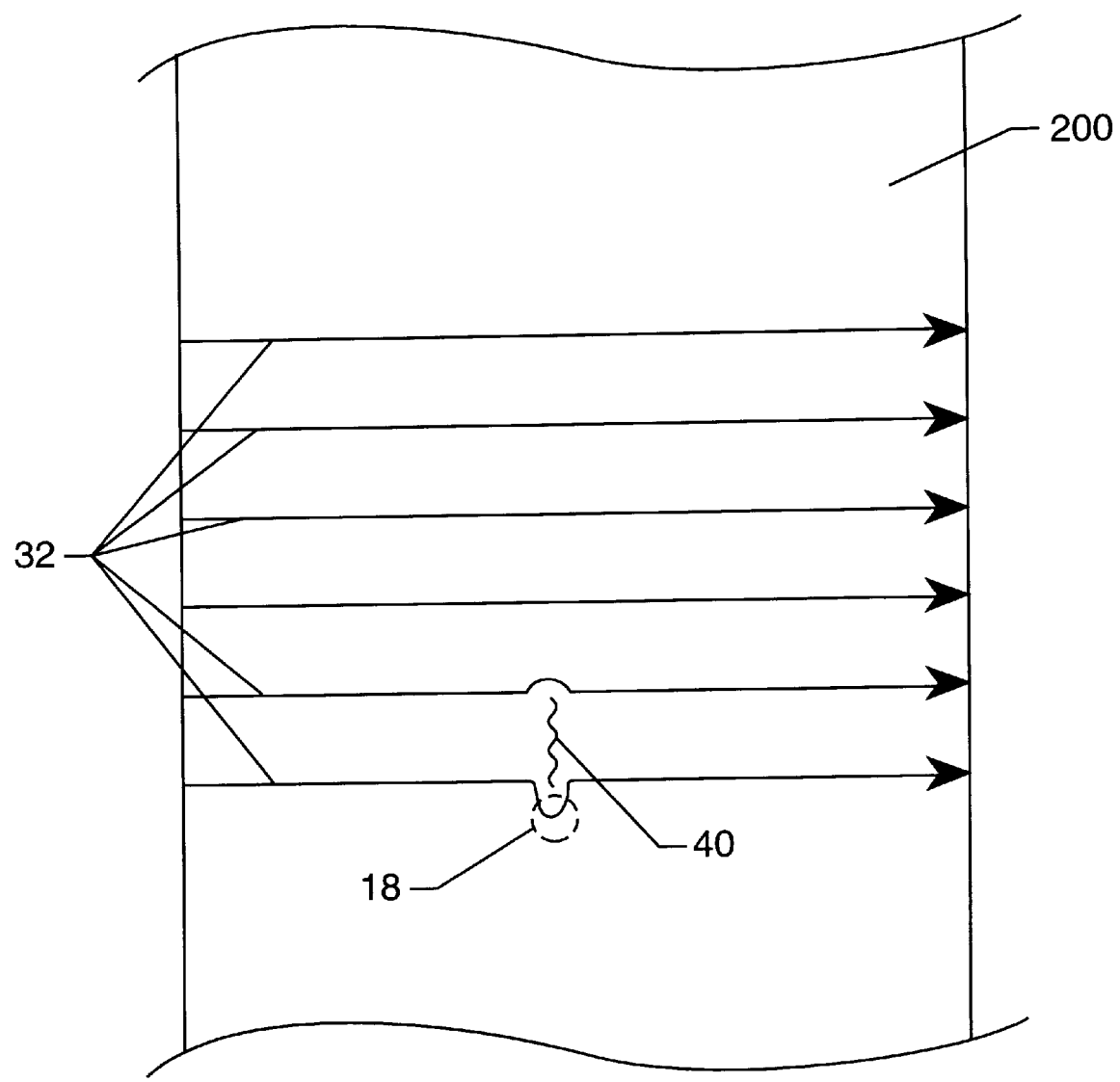
FIG. 3 is a side view of a section of the metal tube having a longitudinal flaw and the path of the resulting circumferential eddy currents induced by the sensor's drive coil.

In operation, sensor 100 is placed inside metal tube 200 such that drive coil 12 is longitudinally aligned there as shown in FIG. 2. In FIGS. 2, 3 and 5–7, AC source 10 and AC voltmeter 16 are omitted for clarity of illustration. Drive coil 12 is energized with current (from AC source 10). For an unflawed section of metal tube 200, magnetic flux represented by lines 30 is focused by conducting material 14. Magnetic flux 30 causes circumferential eddy currents (represented by the circles enclosing the "dots" and "crosses") 32 to flow in metal tube 200. However, since magnetic flux 30 is absorbed by conducting material 14 where it surrounds pick-up coil 18, the flux induced by circumferential eddy currents 32 is not detected by pick-up coil 18. Thus, when no longitudinal flaws are present in metal tube 200, pick-up coil 18 will produce a relatively constant output. However, if a longitudinal flaw is encountered in the area of flux 30, the resulting circumferential eddy currents 32 are forced to circumvent the flaw. This is best seen from the side view of a section of metal tube 200 shown in FIG. 3 having longitudinal flaw or crack 40. When encountering crack 40, circumferential eddy currents 32 follow a detoured path around crack 40. The detoured path causes a portion of eddy currents 32 to cross pick-up coil 18 to effectively link the flux produced by eddy currents 32 with pick-up coil 18. This induces a voltage across pick-up coil 18 which is measured/displayed by, for example, AC voltmeter 16.

Figure 4:
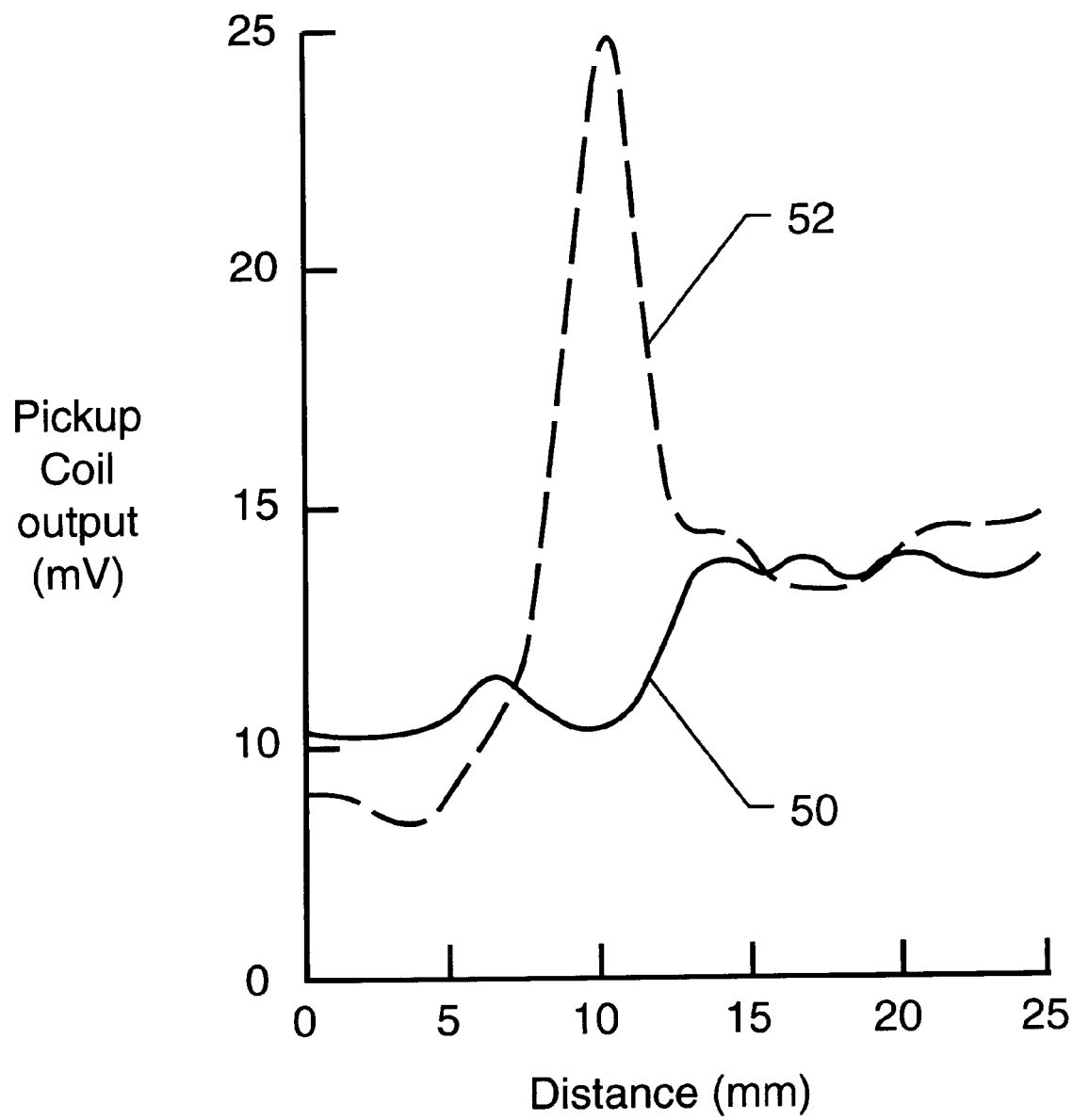
FIG. 4 is a graph depicting the experimental results generated by the sensor of the present invention for both an unflawed and flawed steel tube.
Figure 5:
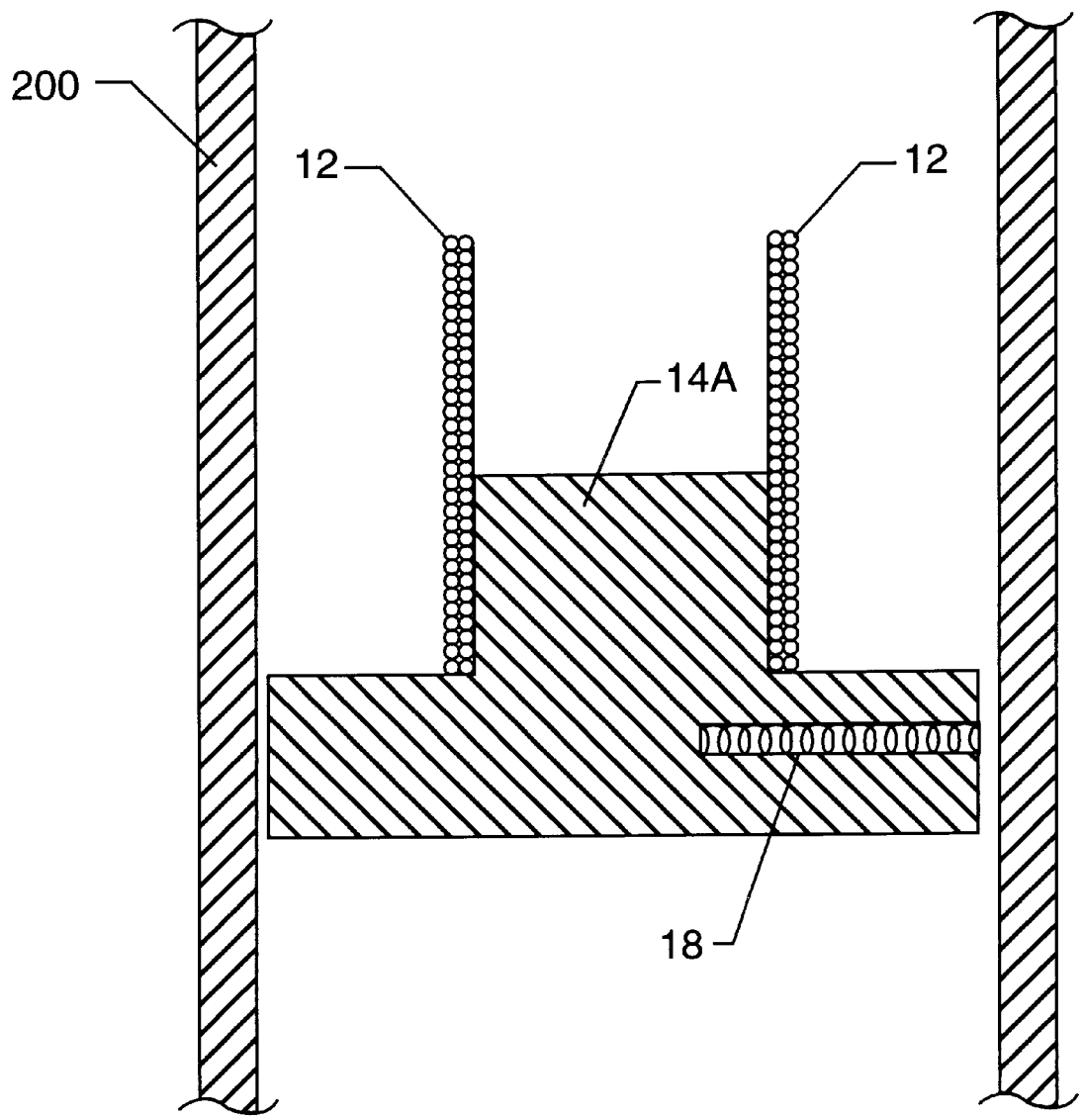
FIG. 5 is another embodiment of the present invention in which the conducting material surrounding the pick-up coil extends only partially into the sensor's drive coil.
Figure 6:
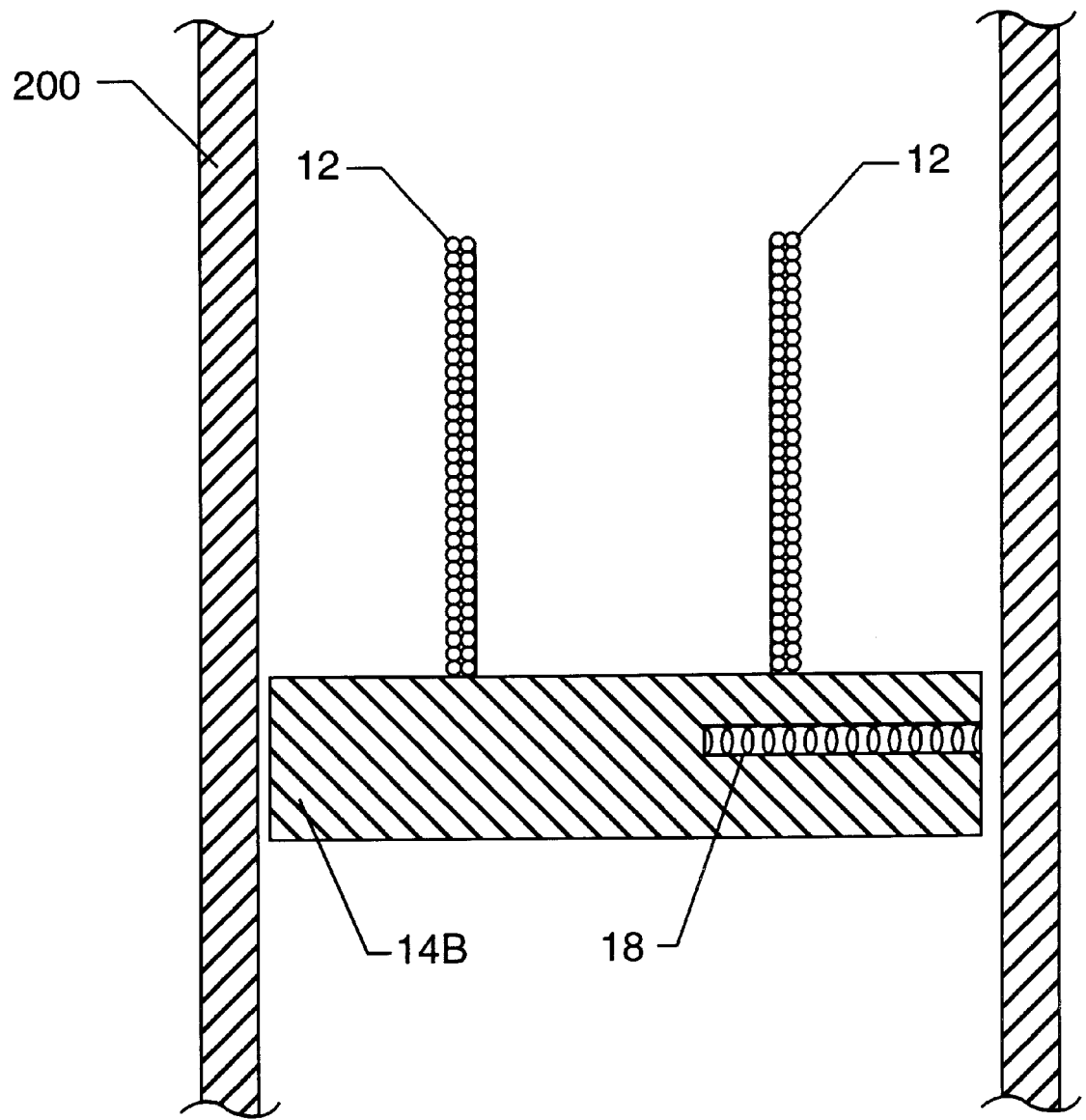
FIG. 6 is another embodiment of the present invention in which the conducting material surrounding the pick-up coil does not extend into the drive coil.

By way of example, the sensor of the present invention was used to examine both an unflawed and flawed steel tube. The flawed tube had a notch that was 0.25 mm wide by 3.175 mm long by 1.57 mm deep at a weld. The operating frequency of the tested sensor was 240 kHz. FIG. 4 shows a graph of the outputs of the sensor's pick-up coil. FIG. 4 is a plot of pick-up coil output (in millivolts) versus the distance (in millimeters) the sensor was moved along the length of the steel tube. Curve 50 is the output for the unflawed tube while curve 52 is the output for the flawed tube. The large peak in curve 52 is unambiguous and clearly shows the location of the flaw.

The advantages of the present invention are numerous. The unambiguous flaw signature of the probe is a major advantage over conventional differential eddy current probes which are currently being used to inspect steel tubing. In practical applications, fatigue damage will normally occur at a joint or support structure and separating the response of the probe due to these structures from that of fatigue damage is not always possible. The unique configuration of the present invention allows it to be sensitive to longitudinal fatigue damage while reducing the effect of other material properties.

Figure 7:
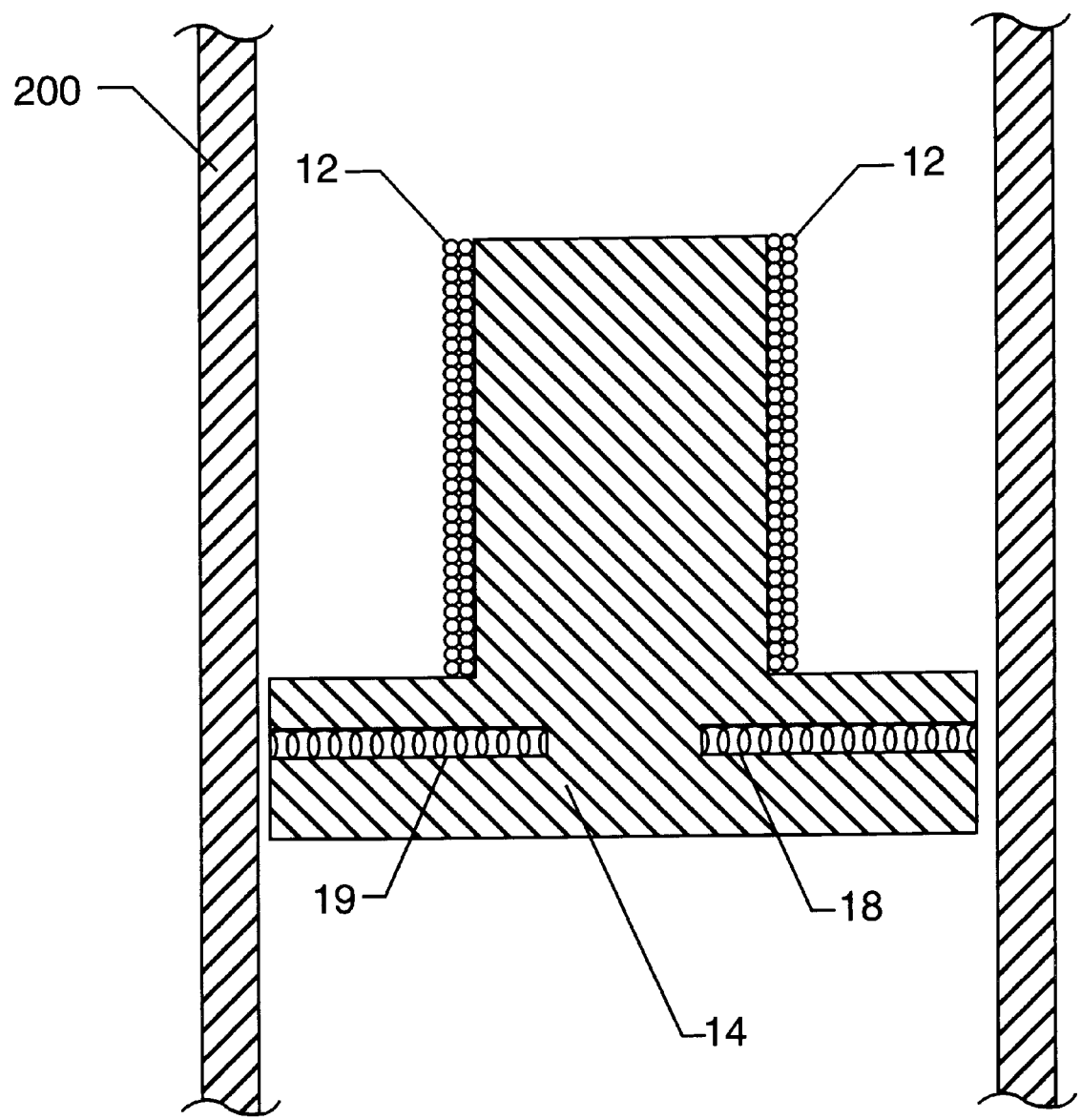
FIG. 7 is yet another embodiment of the present invention in which a plurality of pick-up coils are maintained within the conducting material portion of the sensor.

Although the present invention has been described relative to a specific embodiment, it is not so limited. Several alternative embodiments are presented in FIGS. 5–7 where like reference numerals are used for those elements that are common with the embodiment of FIG. 1. In the embodiment shown in FIG. 5, conducting material 14A extends partially into drive coil 12. In the embodiment shown in FIG. 6, conducting material 14B surrounds pick-up coil 18 but does not extend into drive coil 12, and merely serves as a base for supporting drive coil 12. The reduction or elimination of the extension of the conducting material from within drive coil 12 has the advantage of allowing drive coil 12 to induce stronger circumferential eddy currents in metal tube 200 since the effects of a conductive core on the performance of drive coil 12 are reduced. In another embodiment, the sensor of the present invention can utilize a plurality of pick-up coils. For example, as shown in FIG. 7, a second pick-up coil 19 is shown mounted in conducting material 14 at a position 180° from pick-up coil 18. Such a configuration would be beneficial when examining a metal tube that is welded together from two half sections. Obviously, additional pick-up coils could be mounted in conducting material 14 without departing from the scope of the present invention. Thus, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A radially focused eddy current sensor for detecting longitudinal flaws in a metal tube, comprising:

a drive coil sized for insertion in the metal tube, said drive coil inducing eddy currents within the wall of the metal tube when said drive coil is excited by an alternating current, wherein said drive coil's longitudinal axis is parallel to the wall of the metal tube;

a pick-up coil sized for insertion in the metal tube, said pick-up coil being spaced apart from said drive coil along the length of the metal tube and having a longitudinal axis perpendicular to the longitudinal axis of said drive coil, said pick-up coil having a first end plane and a second end plane and further having a longitudinal axis passing through said first end plane and said second end plane, said first end plane lying adjacent the wall of the metal tube such that said longitudinal axis is perpendicular to the wall of the metal tube; and a flux isolator formed of an electrically conducting material high in magnetic permeability, said flux isolator sized for insertion in the metal tube, said flux isolator surrounding all of said pick-up coil except said first end plane of said pick-up coil, said flux isolator preventing magnetic coupling between said drive coil and said pick-up coil when said sensor is placed within an unflawed metal tube and said flux isolator focusing the magnetic flux produced by said drive coil.

2. An eddy current sensor as in claim 1 wherein said flux isolator extends into said drive coil and is coaxial therewith.

3. An eddy current sensor as in claim 1 wherein said flux isolator extends through said drive coil and is coaxial therewith.

4. An eddy current sensor as in claim 1 wherein said flux isolator includes an extension that extends perpendicular to said longitudinal axis of said pick-up coil, and wherein said drive coil is wound on said extension.

5. An eddy current sensor as in claim 1 wherein said drive coil comprises of at least one layer of wrapped coil windings.

6. An eddy current sensor as in claim 1 wherein said flux isolator has a magnetic permeability of at least 100 and a resistivity of not more than 100 microhm-centimeters.

7. An eddy current sensor as in claim 1 wherein said first end plane of said pick-up coil is closer to the wall of the metal tube than said drive coil.

8. A radially focused eddy current sensor for detecting longitudinal flaws in a metal tube, comprising:

a drive coil sized for insertion in the metal tube, said drive coil inducing eddy currents within the wall of the metal tube when said drive coil is excited by an alternating current, wherein said drive coil's longitudinal axis is parallel to the wall of the metal tube;

a plurality of pick-up coils sized for insertion in the metal tube, each of said plurality of pick-up coils being spaced apart from said drive coil along the length of the metal tube and having a longitudinal axis perpendicular to the longitudinal axis of said drive coil, each of said plurality of pick-up coils having a first end plane and a second end plane and further having a longitudinal axis passing through said first end plane and said second end plane, said first end plane from each of said plurality of pick-up coils lying adjacent the wall of the metal tube such that said longitudinal axis from each of said plurality of pick-up coils is perpendicular to the wall of the metal tube; and a flux isolator formed of an electrically conducting material high in magnetic permeability, said flux isolator sized for insertion in the metal tube, said flux isolator surrounding all of said plurality of pick-up coils except said first end plane of each of said plurality of pick-up coils, said flux isolator preventing magnetic coupling between said drive coil and said pick-up coil when said sensor is placed within an unflawed metal tube and said flux isolator focusing the magnetic flux produced by said drive coil.

9. An eddy current sensor as in claim 8 wherein said flux isolator extends into said drive coil and is coaxial therewith.

10. An eddy current sensor as in claim 8 wherein said flux isolator extends through said drive coil and is coaxial therewith.

11. An eddy current sensor as in claim 8 wherein said flux isolator includes an extension that extends perpendicular to said longitudinal axis of each of said plurality of pick-up coils, and wherein said drive coil is wound on said extension.

12. An eddy current sensor as in claim 8 wherein said drive coil comprises of at least one layer of wrapped coil windings.

13. An eddy current sensor as in claim 8 wherein said flux isolator has a magnetic permeability of at least 100 and a resistivity of not more than 100 microhm-centimeters.

14. An eddy current sensor as in claim 8 wherein each said first end plane of each of said plurality of pick-up coils is closer to the wall of the metal tube than said drive coil.

15. A radially focused eddy current sensor for detecting longitudinal flaws in a metal tube, comprising:

a drive coil sized for longitudinal insertion in the metal tube, wherein said drive coil's longitudinal axis is parallel to the wall of the metal tube;

an alternating current source coupled to said drive coil wherein said drive coil induces eddy currents within the wall of the metal tube when said drive coil receives an alternating current from said alternating current source;

a pick-up coil sized for lateral insertion in the metal tube, said pick-up coil being spaced apart from said drive coil along the length of the metal tube and having a longitudinal axis perpendicular to the longitudinal axis of said drive coil, said pick-up coil having a first end plane and a second end plane and further having a longitudinal axis passing through said first end plane and said second end plane, said first end plane lying adjacent the wall of the metal tube such that said longitudinal axis is perpendicular to the wall of the metal tube;

an electrical measurement device coupled to said pick-up coil for providing an indication of voltage induced across said first end plane; and an electrically conducting material high in magnetic permeability surrounding all of said pick-up coil except said first end plane of said pick-up coil and further extending into said drive coil in a coaxial relationship therewith, said electrically conducting material preventing magnetic coupling between said drive coil and said pick-up coil when said sensor is placed within an unflawed metal tube and said electrically conducting material focusing said eddy currents produced by said drive coil.

16. An eddy current sensor as in claim 15 wherein said electrically conducting material extends through said drive coil.

17. An eddy current sensor as in claim 15 wherein said electrically conducting material includes an extension that extends perpendicular to said longitudinal axis of said pick-up coil, and wherein said drive coil is wound on said extension.

18. An eddy current sensor as in claim 15 wherein said drive coil is a multiple-layer drive coil.

19. An eddy current sensor as in claim 15 wherein said electrically conducting material has a magnetic permeability of at least 100 and a resistivity of not more than 100 microhm-centimeters.

20. An eddy current sensor as in claim 15 wherein said first end plane of said pick-up coil is closer to the wall of the metal tube than said drive coil.

* * * * *